United States Patent [19]

Yafuso et al.

[11] Patent Number: 4,849,172
[45] Date of Patent: Jul. 18, 1989

[54] OPTICAL SENSOR

[75] Inventors: Masao Yafuso, El Toro; Cheng F. Yan, Anaheim; Henry K. Hui, Irvine; William W. Miller, Santa Ana, all of Calif.

[73] Assignee: Minnesota Mining and Manufacturing Company, St. Paul, Minn.

[21] Appl. No.: 148,153

[22] Filed: Jan. 29, 1988

Related U.S. Application Data

[63] Continuation of Ser. No. 853,460, Apr. 18, 1986, abandoned.

[51] Int. Cl.$^4$ ............................................. G01N 21/77
[52] U.S. Cl. .................................... 422/55; 422/56; 422/58; 422/68; 422/83; 422/86; 422/87; 422/91; 436/136; 436/138; 436/167; 436/169; 436/172; 436/178
[58] Field of Search .................. 422/55–58, 422/68, 83, 86, 87, 91; 436/136, 138, 167, 169, 172, 178

[56] References Cited

U.S. PATENT DOCUMENTS

| | | | |
|---|---|---|---|
| 3,725,658 | 4/1973 | Stanley et al. | 436/136 X |
| 4,003,707 | 1/1977 | Lubbers et al. | 436/172 |
| 4,399,099 | 8/1983 | Buckles | 436/136 X |
| 4,557,900 | 12/1985 | Heitzmann | 422/87 X |
| 4,587,101 | 5/1986 | Marsoner et al. | 436/172 X |
| 4,657,736 | 4/1987 | Marsoner et al. | 422/56 |

FOREIGN PATENT DOCUMENTS

| | | |
|---|---|---|
| 0105870 | 4/1984 | European Pat. Off. . |
| 0109959 | 5/1984 | European Pat. Off. . |
| 2132348 | 7/1984 | United Kingdom . |

OTHER PUBLICATIONS

Cox et al., Chemical Abstracts, vol. 103, Abstract No. 103:179010y, 1985.

Primary Examiner—Robert J. Hill, Jr.
Attorney, Agent, or Firm—Gordon L. Peterson; Frank J. Uxa, Jr.

[57] ABSTRACT

An optical sensor which is a gas permeable silicone polymeric matrix having at least one optical indicator therein for providing an optical signal in response to excitation light. The optical indicator essentially comprises a mixture of non-polar derivatives of a polynuclear aromatic compound.

29 Claims, 1 Drawing Sheet

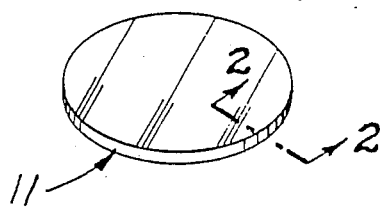
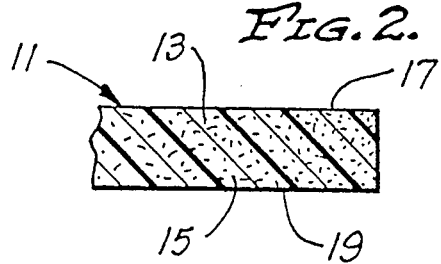
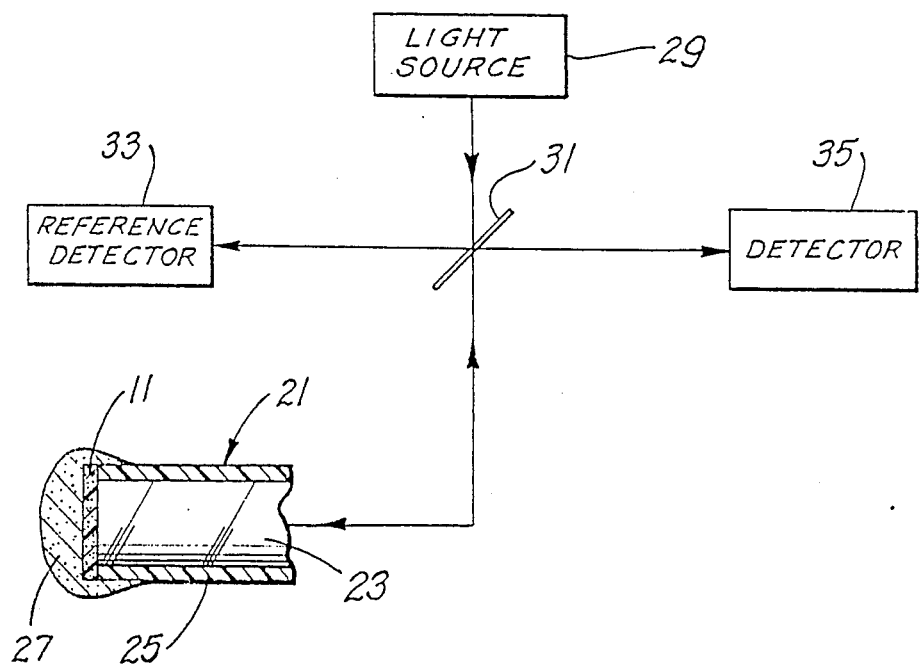

OPTICAL SENSOR

This application is a continuation of application Ser. No. 853,460 filed Apr. 18, 1986, now abandoned.

BACKGROUND OF THE INVENTION

It is sometimes necessary or desirable for a physician to determine the concentration of gases in blood. This can be accomplished utilizing an optical sensor which contains an optical indicator responsive to the constituent of interest. The optical sensor is exposed to the blood, and excitation light is provided to the sensor so that the optical indicator can provide an optical signal indicative of a characteristic of the constituent of interest. For example, the optical indicator may fluoresce and provide a fluorescent optical signal as described in Lubbers et al U.S. Pat. No. RE31,897 or it may function on the principals of light absorbance as described, for example, in Fostick U.S. Pat. No. 4,041,932.

The optical sensor may include a gas permeable polymeric matrix with the optical indicator dispersed in the matrix. For accuracy of measurement, it is important to have a strong optical signal. The intensity of the optical signal is a function of the quantity of the optical indicator present in the polymeric matrix which in turn depends upon the quantity of the optical indicator that can be dissolved in the polymeric matrix during manufacture of the sensor.

Unfortunately, the preferred optical indicators are not very soluble in silicone polymers, the polymers of choice, and so less than the desired quantity of the indicator is present in the matrix. For example, decacyclene is a preferred fluorescent indicator for oxygen because it has maximum sensitivity in the appropriate wavelength range. However, decacyclene is not very soluble in silicone polymers. Silicone polymers are the most suitable oxygen permeable matrix materials known to be presently acceptable for use with blood. Accordingly, the problem cannot be solved by selecting another polymeric matrix material.

It has been suggested by others that the solubility of decacyclene in a silicone polymer might be increased by utilizing the hexa-t-butyl derivative of decacyclene. However, contrary to this suggestion, we have found that the use of hexa-t-butyl decacyclene as a substitute for decacyclene does not, in fact, yield significant and reproducible increases in the solubility in the silicone polymer.

SUMMARY OF THE INVENTION

This invention provides an optical sensor having a higher concentration of the relevant optical indicator in a silicone matrix than has been possible heretofore. Consequently, the optical sensor can provide an optical output signal of higher intensity. The output signal may be fluorescent signal or result from optical absorbance.

These desirable results are accomplished by enhancing the solubility of the optical indicator in a silicone polymeric matrix. This, in turn, can be accomplished by employing as the optical indicator an indicator which consists essentially of a mixture of derivatives of a polynuclear aromatic compound wherein the derivatizing groups are preferably non-polar. Of course, the silicone polymeric matrix may also contain other optical indicators, which are independent of this mixture of derivatives of the polynuclear aromatic compound and additional additives provided for other purposes.

The basic polynuclear aromatic compound suitable for derivation would be any fluorescent or absorbance optical indicator of the polynuclear aromatic class. If used as a fluorescence indicator, for all practical purposes taking into consideration a reasonable cost which would be affordable to hospitals, analytical laboratories and physicians for an analyzing instrument for detecting and analyzing the fluorescent signal, the basic polynuclear aromatic indicator will be chosen such that its excitation wavelength is separated from its fluorescence wavlength by about at least 40 nm (nanometers). Of course, if the analyzing instrumentation costs are not a consideration, the spread between the excitation wavelength and the fluorescence wavelength could be less than 40 nm. In any event, there should not be any overlap of the excitation wavelength and the fluorescence wavelength.

Generally the basic polynuclear aromatic indicator suitable for derivation would be chosen to have an excitation or absorbance wavelength of from about 350 nm to about 450 nm and a fluorescence wavelength of from about 450 nm to about 600 nm.

Presently preferred for the polynuclear aromatic compound suitable for derivation are decacyclene, benzo-ghi-perylene and coronene.

The polynuclear aromatic compound is derivatized with non-polar substituent groups. Alkyl and aromatic hydrocarbons, ketones and ethers are preferred as these substituents. Suitable for use as the substituent group for derivation are aliphatic hydrocarbons, cycloalkyl and cycloalkenyl hydrocarbons, bridge or spiro hydrocarbons, aromatic hydrocarbons and substituted aromatic hydrocarbons, aliphatic-aliphatic ethers, aliphatic-aromatic or substituted aromatic ethers, aromatic or substituted aromatic-aromatic or substituted aromatic ethers, aliphatic-aliphatic ketones, aliphatic-aromatic or substituted aromatic ketones and aromatic or substituted aromatic-aromatic or substituted aromatic ketones where the aliphatic groups are chosen from the group consisting of $C_1$-$C_{18}$ straight and branched chain alkyl, alkenyl and alkynyl hydrocarbons and the substituent groups for the aromatic hydrocarbons are chosen from the group consisting of alkyl, alkenyl, alkynyl, fluoro and chloro.

Thus a preferred group of said non-polar derivatives are chosen from the group consisting of aliphatic hydrocarbons, cycloalkyl and cycloalkenyl hydrocarbons, alkyl and alkenyl spiro hydrocarbons, aromatic hydrocarbons, aliphatic-aliphatic ethers, aliphatic-aromatic ethers, aromatic-aromatic ethers, aliphatic-aliphatic ketones, aliphatic-aromatic ketones and aromatic-aromatic ketones where said aliphatic hydrocarbons, ethers and ketones are $C_1$-$C_{18}$ straight and branched chain alkyl, alkenyl and alkynyl hydrocarbons, ethers and ketones, respectively, and said aromatic hydrocarbons, ethers and ketones are un-substituted and substituted aromatic hydrocarbons are alkyl, alkenyl, alkynyl, fluoro and chloro.

A more preferred group of said non-polar derivatives would be chosen from the group consisting of aliphatic hydrocarbons, cycloakyl and cycloalkenyl hydrocarbons, alkyl and alkenyl spiro hydrocarbons, aromatic hydrocarbons and substituted aromatic hydrocarbons where said aliphatic hydrocarbons are $C_1$-$C_{18}$ straight and branched chain alkyl, alkenyl and alkynyl hydrocarbons and where said substituted aromatic hydrocarbons are alkyl, alkenyl, alkynyl, fluoro and chloro substituted aromatic hydrocarbons.

According to this invention, the precursor polynuclear aromatic compound is derivatized to provide a mixture of a plurality of derivatives. For the purposes of this specification, mixtures of derivatives are defined as meaning multiples of the same substituent, multiples of different substitutents and isomeric mixtures. As an example of multiples of the same substitutent would be instances in which decacyclene is derivatized with t-butyl groups to yield a mixture of hexa-t-butyl decacyclene, penta-t-butyl decacyclene, decacyclene and tetra-t-butyl decacyclene shown in scheme A. As an example of multiples of different substituents are mixtures similar to those of the preceding sentence except two different derviation groups are used as for instance the t-butyl group and the isopentyl group. In addition multiple isomers of the same group can also be formed. Examples of these would be the isomers of tri-t-butyl decacyclene shown in scheme B and those of tetra-t-butyl decacyclene shown in scheme C.

These mixtures are formed by reacting the basic polynuclear aromatic compound with the precursor of the derivative group or groups in a manner wherein there is incomplete substitution of all the possible substitution sites on the basic polynuclear aromatic compound. This can generally be accomplished by conducting an incomplete reaction. A first way of achieving this result is by utilizing less than the amount of the precursor of the derivative group which is necessary to completely substitute the basic polynuclear aromatic compound. A further way is to run the substitution reaction for a time period which is insufficient for complete reaction, and an additional way is to run the reaction at a depressed temperature so as to retard the rate of the reaction. In any event the reaction will be conducted in such a manner that mixtures of products of the substitution of the basic polynuclear aromatic compound are obtained.

It has been found that by using mixtures of these derivatives of the polynuclear aromatic compounds that the solubility of the polynuclear aromatic compounds are greatly enhanced. For example, utilizing a mixture of derivatized decacyclene, the solubility has been increased to about at least two to ten fold as compared with the solubility of underivatized decacyclene in the same silicone polymer. The results achieved with this invention are synergistic in that the solubility of the mixtures of derivatives of the polynuclear aromatic compounds in a silicone polymeric matrix is much greater than the solubility of the individual compound in the same polymeric matrix. The solubility of the compound is enhanced by using mixtures of derivatives and/or isomers of the compound.

The reason why the mixtures of these derivatives enhances the solubility in a silicone polymeric matrix is not known for certain. While we do not wish to be bound by theory, it is believed that a pure compound has a higher crystallization energy and it is further believed that the multiple derivatives and/or isomers interfere with the fitting together of the individual molecules in the crystal lattice structure. It is believed that this is one contributing factor leading to the enhanced solubility.

A significant advantage of this invention is that each of the mixtures of derivatives of the polynuclear aromatic compounds have similar optical properties for providing an optical signal in response to excitation light. For example, in the case of decacyclene, which is a fluorescent indicator, each of the mixtures of derivatives thereof provided in accordance with the teachings of this invention have similar excitation and emission wavelengths. If this were not the case, the optical properties of the sensor would tend to be much more varied.

Although various forms of silicone can be employed for the matrix, it is important that the silicone have a high permeability to the gas of interest so that the sensitivity of the optical indicator to the gas of interest is optimized. For example, the silicone polymer may be dimethylsiloxane, diphenylsiloxane, or a diphenyldimethylsiloxane copolymer. Of this group, dimethylsiloxane is preferred because of its high gas permeability. It is of course realized that other members of the homologous series which include the before mentioned polymers might also be used.

An optical sensor constructed in accordance with the teachings of this invention has a higher concentration of the optical indicator in the silicone polymeric matrix and as a result thereof, the optical output signal obtainable from the optical indicator is also higher. For example, using the mixtures of derivatives of polynuclear aromatic compounds of this invention, up to five times more optical indicator can be dissolved in a given weight of a silicone polymer as compared with utilizing any of the individual compounds alone. Similarly, using the features of this invention, the optical signal is up to about five times stronger as compared with the optical signal generated from the individual compounds in the silicone polymer.

The mixtures of derivatives of the polynuclear aromatic compounds can be obtained using synthesizing procedures, such as a Friedel-Craft reaction. The mixtures of the polynuclear aromatic compounds thus obtained can then be dispersed in an uncured silicone as a powder or in a volatile solvent such as methylene chloride or hexane. The solvent is then removed as for instance by vacuum evaporation or the like. The uncured silicone having the mixture of derivatives of the polynuclear aromatic compound dispersed therein, is then crosslinked to form the optical sensor.

Solubility of the derivatives in the silicone polymer can be also be enhanced by appropriately controlling the number and ratio of the derivatives of the polynuclear aromatic compound in the mixture. Heretofore utilizing only hexa-t-butyl decacyclene it was only possible to obtain a concentration of the hexa-t-butyl decacyclene no greater than 0.5 mg per gram of dimethylsiloxane silicone polymer. Utilizing the teaching of this invention, solubilities of at least 1.2 mg per gram of gas permeable silicone polymer, such as dimethylsiloxane, can be achieved. However, even greater solubilities of 4 to 5 mg per gram of silicone polymer have been achieved. In this regard, for decacyclene, it is preferred to utilize a mixture having at least three derivatives of the basic decacyclene compound as determined by liquid chromatography. A typical ratio for the three derivatives of decacyclene would be approximately 51 to 45 to 3 as determined by liquid chromatography. Typically, this ratio would have a solubility of about 4 mg per gram of the silicone polymer.

BRIEF DESCRIPTION OF THE DRAWINGS

FIG. 1 is a perspective view of an optical sensor constructed in accordance with the teachings of this invention.

FIG. 2 is an enlarged, fragmentary, sectional view taken generally along line 2—2 of FIG. 1.

FIG. 3 is a schematic view partially in section showin an apparatus for providing continuous monitoring of substances in the blood with such apparatus incorporating the optical sensor of this invention.

DESCRIPTION OF THE PREFERRED EMBODIMENT

FIG. 1 shows an optical sensor 11 which comprises a matrix 13 (FIG. 2) of a silicone polymer and an optical indicator 15 dissolved in and carried by the matrix. Although the matrix 13 can be of various sizes and configurations, in the form shown in FIGS. 1-3, the matrix is in the form of a thin, cylindrical membrane having relatively broad circular faces 17 and 19.

Although the sensor 11 may sense various blood constituents, such as oxygen and carbon dioxide, in this embodiment, it is an oxygen sensor. Accordingly, the matrix 13 is constructed of an oxygen permeable material, such as a silicone polymer. Similarly, the optical indicator 15 must be oxygen responsive and may be, for example, derivatives of decacyclene.

The optical sensor 11 can be used in various different ways to measure the concentration of oxygen in blood or other substances. For example, the optical sensor 11 may be suitably retained on a distal end of an optical fiber 21 as by mechanical means (not shown), by adhesion of the silicone of the sensor to the fiber and/or by use of an adhesive. The optical fiber 21 includes a core 23 and cladding 25 and an opaque overcoat 27 of cellulose or other oxygen-permeable material covering the optical sensor 11 at a distal end portion of the optical fiber 21. The overcoat 27 may also be used to retain or to assist in retaining the optical sensor 11 on the optical fiber 21.

Although the optical sensor 11 could function on the principles of absorbance, in this embodiment, the sensor is a fluorescent sensor. Exciting light from a light source 29 is directed towards a half-silvered mirror 31, and a component of the exciting light is reflected by the mirror to a reference detector 33. The remainder of the exciting light passes through the mirror 31 and through the optical fiber 21 to the sensor 11. The reference detector 33 compensates for variations in intensity of the light source 29.

The exciting light excites the fluorescence of the optical indicator 15. If the optical sensor 11 is in the presence of oxygen gas, the optical indicator 15 emits a fluorescent light signal at a different wavelength from the exciting light of the source 29 with the intensity of the signal depending on the concentration of the oxygen. The fluorescent signal returns through the optical fiber 21 to the mirror 31 which reflects a component of the fluorescent signal to a detector 35 which measures the intensity of the fluorescent signal and correlates that to oxygen concentration in the sample being tested.

The optical fiber 21 may be in the form of probe or catheter insertable into a blood vessel of a patient to provide continuous on-line in vivo monitoring of oxygen gas concentration in the blood. Alternatively, the optical sensor 11 can be embodied in a flow-through housing as shown, for example, in Heitzmann U.S. Pat. No. 4,557,900 to provide extracorporeal blood gas monitoring.

EXAMPLES

Example 1

4.5 grams of decacyclene were added to a 500 cc. flask equipped with a drying tube and a magnetic stirring rod. 450 mls of o-dichlorobenzene and 15 mls of t-butyl chloride were added. The reaction mixture was rapidly stirred. Approximately 400 mg (weighed by difference) of aluminum chloride was added to the reaction. Upon the addition of the aluminum chloride, the color of the reaction mixture changed from brown to greenish brown. The reaction was allowed to proceed overnight.

The reaction was quenched with 100 cc of a 3% sodium hydroxide solution. The organic phase was separated and the aqueous phase was extracted with dichloromethane. The combined organic phases were washed once with water and the solvent was evaporated on a rotary evaporator under vacuum.

The crude reaction product was loaded onto a 4×24 inch chromatography column containing 1100 grams of silica gel. Utilizing hexane as the mobile phase, a yellow fluorescent eluent was collected. The solvent was evaporated under vacuum to yield approximately 3.5 grams of crystals.

The crystals were extracted with 100 cc of hexane per 3 grams of crystals by stirring at room temperature for 0.5 hours. The insoluble fractions were removed by filtering, and the filtrate was evaporated to yield 1.5 grams of final product. HPLC was utilized to monitor the reaction, the purification steps and the final product. The final product was shown by HPLC to be a mixture of derivatives believed to be hexa-t-butyl decacyclene, penta-t-butyl decacyclene and tetra-t-butyl decacyclene in a ratio of 51 to 45 to 3, respectively, as determined by liquid chromatography.

Example 2

In a like manner to Example 1, 1 gram of decacyclene was suspended in 40 cc of o-dichlorobenzene. 2.0 grams of aluminum chloride followed by 4.0 grams of chlorobenzyl chloride were added with stirring. The reaction mixture was allowed to react for 40 minutes at ambient temperature and then was quenched with dilute sodium hydroxide. The organic phase was washed once with dilute sodium bicarbonate solution and then evaporated under vacuum to yield a brownish oily suspension. This oil was purified on a silica gel column using methylene chloride as the eluent to yield 0.5 grams of yellowish brown crystals.

Example 3

In a like manner to Example 1, to 150 mg of benzo-ghi-perylene in 30 cc of o-dichlorobenzene was added 0.15 grams of aluminum chloride and 0.5 grams of t-butyl chloride. The reaction mixture was stirred for four hours and quenched. The organic phase was evaporated and the residue passed through a silica gel column to yield 125 mg of yellow crystals.

Example 4

In a like manner to Example 1, isopentyl chloride was reacted with decacyclene.

Example 5

In a like manner to Example 1, 3-chloro-3-methylpentane was reacted with decacyclene.

Example 6

In a like manner to Example 1, ethylbromide was reacted with decacyclene.

Example 7

In a like manner to Example 1, beta-chloro-p-fluoropropiophenone was reacted with decacyclene to yield a fluorescent tar.

Example 8

In a like manner to Example 1, exonorborneol was reacted with decacyclene.

Example 9

In a like manner to Example 1, 2-chloroethylvinylether was reacted with decacyclene.

Example 10

In a like manner to Example 1, adamantylethanol was reacted with decacyclene.

Example 11

In a like manner to Example 1, 1-adamantylmethanol was reacted with decacyclene.

Example 12

In a like manner to Example 1, 2-chlorobutane was reacted with decacyclene.

Example 13

In a like manner to Example 1, 2-chloropropane was reacted with decacyclene.

Example 14

In a like manner to Example 1, chlorocyclohexane was reacted with decacyclene.

Example 15

In a like manner to Example 1, chloroethane was reacted with decacyclene.

Example 16

In a like manner to Example 1, equal mixtures of t-butyl chloride, 2-chloropropane, 2-chlorobutane and chlorocyclohexane were reacted with decacyclene.

Example 17

In a like manner to Example 1, 1-chloro-hex-3-yne was reacted with decacyclene.

Typically, utilizing t-butyl chloride for an example, for each 4.5 grams of decacyclene, 8 to 20 grams of t-butyl chloride would be used, 0.2 to 0.6 grams of aluminum chloride would be used and 300 to 700 cc of o-dichlorobenzene would be used.

In a like manner suitable mixtures of derivatives could be prepared utilizing 2-chloroethylbenzene, 1-chlorooctadecane, 1-chlorododecane, norbornylene, 2-chloroethylethylether, crotyl chloride, allyl chloride, propargyl chloride, chloroacetophenone and chloroethylphenyl ketone by reacting the same with a suitable polynuclear aromatic compound such as decacyclene, benzo-ghi-perylene or coronene.

Example 18

300 mg of a mixture of t-butylated decacyclene derivatives were dissolved in 15 cc of hexane to form a solution. The solution was mixed with 100 grams of vinyl terminated dimethylsilicone. The mixture was stirred until a clear homogeneous solution was obtained. The solvent was removed under vacuum. The residue was further cross linked to yield an optical sensor having a mixture of derivatives of a polynuclear aromatic compound in a silicone polymer matrix.

Example 19

A optical sensor was constructed as per Example 19 utilizing the mixture of derivatives of Example 1. For this sensor 0.3 grams of the mixture of derivatives of Example 1 were initially solubilized in 100 grams of the dimethylsiloxane precursor. As a result, an optical sensor of the type shown in FIG. 1 was produced. Exciting light at a wavelength of 400 nm was directed at the optical sensor when the sensor was in the presence of oxygen gas having a concentration of 74 mm Hg to provide a fluorescent signal having a peak at a wavelength of 510 nm.

Although exemplary embodiments of the invention have been shown and described, many changes, modification and substitutions may be made by one having ordinary skill in the art without necessarily departing from the spirit and scope of this invention.

SCHEME A

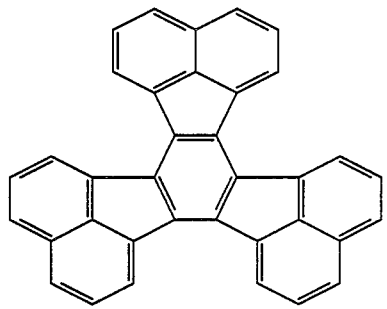

Decacyclene

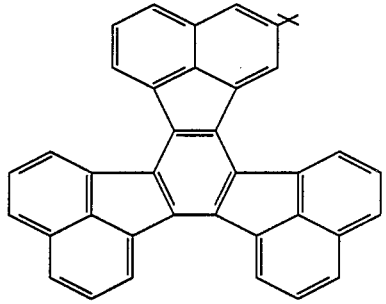

mono-t-butyl-decacylene

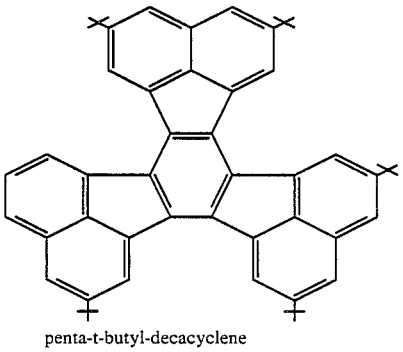

penta-t-butyl-decacyclene

-continued

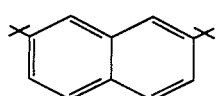
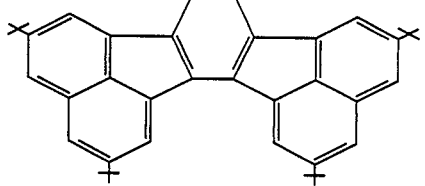
hexa-t-butyl-decacyclene

SCHEME B

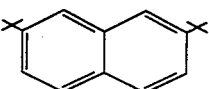
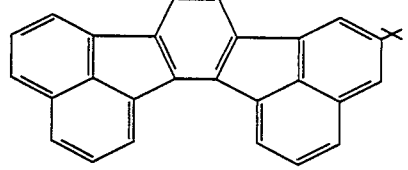

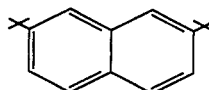
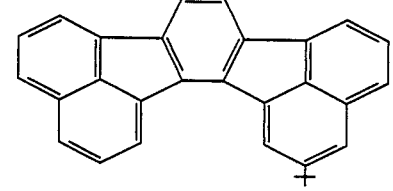

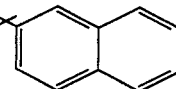
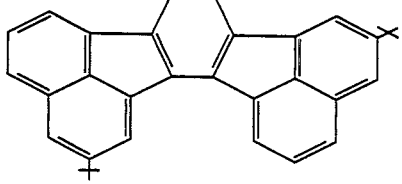
tri-t-butyl-decacyclene

SCHEME C

-continued

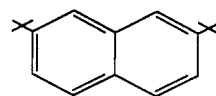
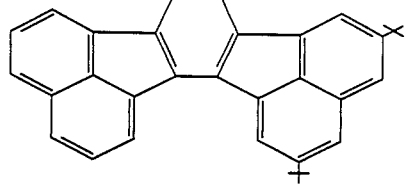

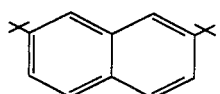
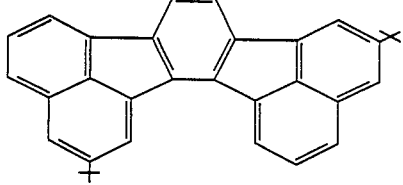

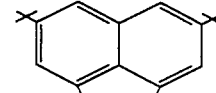
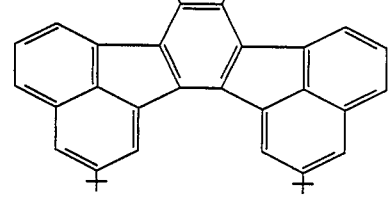

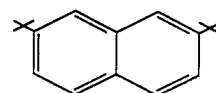
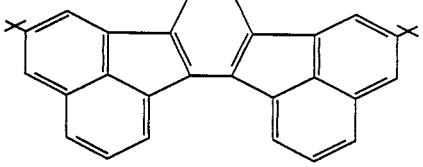
tetra-t-butyl-decacyclene t-butyl group = +

We claim:
1. An optical sensor for a blood constituent of interest consisting essentially of:
a gas permeable, crosslinked silicone polymeric matrix having therein at least one optical indicator consisting essentially of a mixture of derivatives of a polynuclear aromatic compound, each of said derivatives providing a portion of an optical signal in response to excitation light when in the presence of a blood constituent of interest.
2. A sensor of claim 1 wherein:

said polynuclear aromatic compound is selected from the group consisting of decacyclene, benzo-ghi-perylene and coronene.

3. A sensor of claim 1 wherein:
said polynuclear aromatic compound is decacyclene.

4. A sensor of claim 1 wherein said polynuclear aromatic compound is derivatized with at least one material selected from the group consisting of aliphatic hydrocarbons, cycloalkyl and cycloalkenyl hydrocarbons, alkyl and alkenyl spiro hydrocarbons, aromatic hydrocarbons, aliphatic-aliphatic ethers, aliphatic-aromatic ethers, aromatic-aromatic ethers, aliphatic-aliphatic ketones, aliphatic-aromatic ketones and aromatic-aromatic ketones; provided that said aliphatic groups are selected from the group consisting of $C_1$-$C_{18}$ straight and branched chain alkyl, alkenyl and alkynyl groups, and said aromatic groups are selected from the group consisting of unsubstituted and substituted aromatic groups where said substituents on said substituted aromatic groups are selected from the group consisting of alkyl, alkenyl, fluoro and chloro groups.

5. A sensor of claim 4 wherein:
said at least one material is selected from the group consisting of aliphatic hydrocarbons, cycloalkyl and cycloalkenyl hydrocarbons, alkyl and alkenyl spiro hydrocarbons, aromatic hydrocarbons and substituted aromatic hydrocarbons; provided that said aliphatic groups are selected from the group consisting of $C_1$-$C_{18}$ straight and branched chain alkyl, alkenyl, and alkynyl groups, and said substituents on said substituted aromatic groups are selected from the group consisting of alkyl, alkenyl alkynyl, fluoro and chloro groups.

6. A sensor of claim 1 wherein:
said derivatives are non-polar derivatives.

7. A sensor of claim 1 wherein:
said mixture of derivatives of said polynuclear aromatic compound is a mixture of t-butyl derivatives of said polynuclear aromatic compound.

8. A sensor of claim 7 wherein:
said polynuclear aromatic compound is decacyclene and said mixture is soluble in hexane.

9. A sensor of claim 8 wherein:
said silicone polymeric matrix is a dimethylsiloxane polymeric matrix.

10. A sensor of claim 1 wherein:
said silicone polymeric matrix is selected from the group consisting of dimethylsiloxane, diphenylsiloxane and dimethyldiphenylsiloxane.

11. A sensor of claim 1 wherein:
said mixture of derivatives of said polynuclear aromatic compound includes at least three derivatives of said polynuclear aromatic compound.

12. A sensor of claim 1 wherein:
said mixture of derivatives of said polynuclear aromatic compound is present in said silicone polymeric matrix in a concentration of at least about 1.2 mg of said mixture per gram of said silicone polymeric matrix.

13. An optical sensor consisting essentially of:
a gas permeable, crosslinked dimethylsiloxane polymeric matrix having a mixture of t-butyl derivatives of decacyclene present therein.

14. The sensor of claim 13 wherein:
said mixture of derivatives includes at least three of said derivatives and is soluble in hexane.

15. The sensor of claim 13 wherein:
said mixture is present in an amount of least 1.2 mg of said mixture per gram of said polymeric matrix.

16. An apparatus for measuring a blood constituent of interest consisting essentially of:
an optical sensor consisting essentially of a gas permeable, crosslinked silicone matrix having therein at least one optical indicator consisting essentially of a mixture of derivatives of a polynuclear aromatic compound, each of said derivatives providing a portion of an optical signal in response to excitation light when exposed to a blood constituent of interest, said matrix being permeable to such a blood constituent of interest;
means for holding the optical sensor so that it can be exposed to blood; and
optical fiber means for delivering excitation light to the optical sensor so that the optical sensor can provide an optical signal indicative of a characteristic of a constituent of interest and of transmitting such an optical signal from the optical sensor.

17. The apparatus of claim 16 wherein:
said derivatives are hydrocarbon derivatives.

18. The apparatus of claim 16 wherein:
said at least one optical indicator consists essentially of a mixture of derivatives of decacyclene.

19. The apparatus of claim 18 wherein:
said derivatives are t-butyl derivatives and said mixture is soluble in hexane.

20. An optical sensor for a blood constituent of interest consisting essentially of:
a gas permeable, crosslinked silicone polymeric matrix having at least one optical indicator therein for providing an optical signal in response to excitation light when in the presence of a blood constituent of interest, said at least one optical indicator consisting essentially of a mixture of derivatives of a polynuclear aromatic compound selected from the group consisting of decacyclene, benzo-ghi-perylene and coronene.

21. A sensor of claim 20 wherein said polynuclear aromatic compound is decacyclene.

22. A sensor of claim 21 wherein said derivatives are t-butyl derivatives.

23. A sensor of claim 22 wherein said silicone polymeric matrix is a dimethylsiloxane polymeric matrix.

24. A sensor of claim 20 wherein said polynuclear aromatic compound is benzo-ghi-perylene.

25. A sensor of claim 24 wherein said derivatives are t-butyl derivatives.

26. An optical sensor consisting essentially of a gas permeable, crosslinked dimethylsiloxane polymeric matrix having an optical indicator consisting essentially of a mixture of derivatives of a polynuclear aromatic compound selected from the group consisting of decacyclene, benzo-ghi-perylene and coronene dispersed therein, said optical indicator being present in an amount of at least about 1.2 mg of said indicator per gram of said dimethylsiloxane polymerix matrix.

27. An apparatus for measuring a blood constituent of interest consisting essentially of:
an optical sensor consisting essentially of a gas permeable, crosslinked silicone matrix having at least one optical indicator therein for providing an optical signal in response to excitation light when exposed to a blood constituent of interest, said at least one optical indicator consisting essentially of a mixture of derivatives of a polynuclear aromatic compound selected from the group consisting of decacyclene, benzo-ghi-perylene and coronene, said matrix being permeable to such a blood constituent of interest;

means for holding the optical sensor so that it can be exposed to blood; and optical fiber means for delivering excitation light to the optical sensor so that the optical sensor can provide an optical sensor indicative of a characteristic of a constituent of interest and for transmitting such an optical signal from the optical sensor.

28. The apparatus of claim 27 wherein:
said at least one optical indicator consists essentially of derivatives of decacyclene.

29. The apparatus of claim 28 wherein said derivatives are t-butyl derivatives.

* * * * *

UNITED STATES PATENT AND TRADEMARK OFFICE
CERTIFICATE OF CORRECTION

PATENT NO. : 4,849,172
DATED : July 18, 1989
INVENTOR(S) : Yafuso et al

It is certified that error appears in the above—identified patent and that said Letters Patent is hereby corrected as shown below:

Column 1, line 57 after "be" insert -- a --.

Column 2, line 57 after "aromatic hydrocarbons" insert -- , ethers and ketones, respectively, where said substitution substituents on said substituted aromatic hydrocarbons --

Column 4, line 41 change "be also" to -- also --.

Column 4, line 67 change "showin" to -- showing --.

Signed and Sealed this

Twelfth Day of June, 1990

*Attest:*

HARRY F. MANBECK, JR.

*Attesting Officer*     *Commissioner of Patents and Trademarks*